(12) United States Patent
Freeman

(10) Patent No.: US 7,375,235 B2
(45) Date of Patent: May 20, 2008

(54) PROCESS FOR PREPARING SUBSTITUTED BENZIMIDAZOLE COMPOUNDS

(75) Inventor: Stephen Freeman, High Wycombe (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 218 days.

(21) Appl. No.: 11/190,581

(22) Filed: Jul. 26, 2005

(65) Prior Publication Data

US 2005/0261211 A1 Nov. 24, 2005

Related U.S. Application Data

(62) Division of application No. 10/240,906, filed as application No. PCT/EP01/04080 on Apr. 10, 2001, now Pat. No. 7,101,994.

(30) Foreign Application Priority Data

Apr. 11, 2000 (GB) ................. 0008939.1

(51) Int. Cl.
*C07D 234/02* (2006.01)
*A61K 31/70* (2006.01)

(52) U.S. Cl. ............... 548/302.7; 536/27.311; 536/28.9; 514/43; 514/394; 514/396

(58) Field of Classification Search ........... 514/396, 514/43, 394; 536/27.13; 548/302.7
See application file for complete search history.

(56) References Cited

U.S. PATENT DOCUMENTS

| | | | |
|---|---|---|---|
| 5,003,079 A | 3/1991 | Meier et al. | |
| 5,998,605 A | 12/1999 | Chamberlain et al. | |
| 6,077,832 A | 6/2000 | Chamberlain et al. | |
| 6,307,043 B1 | 10/2001 | Chamberlain et al. | |
| 6,455,507 B1 | 9/2002 | Drach et al. | |
| 6,469,160 B1 | 10/2002 | Glover et al. | |
| 6,482,939 B1 | 11/2002 | Hodgson et al. | |

FOREIGN PATENT DOCUMENTS

| WO | WO 90/15058 | 12/1990 |
|---|---|---|
| WO | WO 92/07867 | 5/1992 |
| WO | WO 93/18009 | 9/1993 |
| WO | WO 96/01833 | 1/1996 |
| WO | WO 96/07646 | 3/1996 |
| WO | WO 97/07125 | 2/1997 |
| WO | WO 97/25316 | 7/1997 |
| WO | WO 97/25337 | 7/1997 |
| WO | WO 97/27204 | 7/1997 |
| WO | WO 98/35977 | 8/1998 |
| WO | WO 98/56761 | 12/1998 |
| WO | WO 99/06424 | 2/1999 |
| WO | WO 99/51617 | 10/1999 |
| WO | WO 99/51618 | 10/1999 |
| WO | WO 00/05231 | 2/2000 |

OTHER PUBLICATIONS

Giradet, J.L., et al. "Synthesis of β-L-Lyxofuranosyl Benzimidazoles by an Unexpected Intramolecular Displacement Reaction." J. Org. Chem. 1999, 64, 4169-4172.
Kawashima, E., et al. "2,5,6-Trichlorobenzimidazole. Synthesis of a precursor for 2-substituted 5,6-dichlorobenzimidazoles." Nucleic Acid Chem. (1991), 4 24-6. Section 1, Heterocyclic Compounds.
Schwiebert, K.E., et al. "Engineering the Solid State with 2-Benzimidazolones." J. Am. Chem. Soc. 1996, 118, 4018-4029.
Townsend, L.B., et al. "Design, Synthesis, and Antiviral Activity of Certain 2,5,6-Trihalo-1-(β-D-Ribofuranosyl)Benzimidazoles." J. Med. Chem. 1995, 38, 4098-4105.
Rykowski, A., et al. "Ring Transformations and Amination in Reactions of 3-Halogeno-5-phenyl-1,2,4-triazines with Potassium Amide in Liquid Amonia." J. Org. Chem. 1980, 45, 881-885.
Sakamoto, T., et al. "Palladium-Catalyzed Cross-Coupling Reaction of Haloazoles with Phenylsulfonylacetonitrile." Synthesis, Short Papers, Jun. 1992, pp. 552-554.
Wright, W.B. Jr., "N,N'-Carbonyldiimidazole as a Reagent for the Preparation of Five-Membered Heterocyles." Journal of Heterocyclic Chemistry, 1965, 2(1), pp. 41-43.
Gudmundsson, K.S., et al. "Synthesis and Antiviral Activity of Certain 5'-Modified Analogs of 2,5,6-Trichloro-1-(beta-D-ribofuranosyl) Benzimidazole." Journal of Medicinal Chemistry, vol. 40, No. 5, pp. 785-792, Feb. 28, 1997.
Jui, J., et al. "Synthesis in the 1,2,4-Benzotriazine Series." Journal of Organic Chemistry, Jul. 14, 1959, vol. 24, No. 6, pp. 813-818.

*Primary Examiner*—James O. Wilson
*Assistant Examiner*—Paul V. Ward
(74) *Attorney, Agent, or Firm*—R. Steve Thomas

(57) ABSTRACT

The invention relates to new methods of preparing substituted benzimidazole compounds, such as 2-bromo-5,6-dichlorobenzimidazole, which are useful in the preparation of compounds having antiviral activity.

5 Claims, No Drawings

PROCESS FOR PREPARING SUBSTITUTED BENZIMIDAZOLE COMPOUNDS

CROSS-REFERENCES TO RELATED APPLICATIONS

This application is a divisional of U.S. Ser. No. 10/240,906, filed 5 Feb. 2003, now U.S. Pat. No. 7,101,994 which is a Rule 371 Application of PCT Application No. EP01/04080, filed 10 Apr. 2001, which claims priority to GB Application Serial No. 0008939.1, filed 11 Apr. 2000.

BACKGROUND OF THE INVENTION

The present invention relates to new processes for the preparation of substituted benzimidazole compounds.

Certain substituted benzimidazole nucleosides have been shown to possess antiviral activity. PCT Publication No. WO 98/56761 teaches a series of substituted benzimidazole pyranosyls having antiviral activity, and processes for preparing the same. PCT Publication Nos. WO 92/07867, 96/01833, 97/25337, 99/06424 teach a series of substituted benzimidazole furanosyls, including substituted benzimidazole furanosyls having antiviral activity, and processes for preparing the same.

U.S. Pat. No. 5,003,079 is directed toward a process for the preparation of benzimidazolones. E. Kawashima, et al. *Heterocyclic Compounds* 4:24-26 (1991), relates to a process for preparing 2,5,6-trichlorobenzimidazole. L Townsend, *J. Med. Chem.* 38:4098 (1995), relates to a process for synthesizing certain 2,5,6-trihalo-1-(β-D-ribo-furanosyl)benzimidazoles.

SUMMARY OF THE INVENTION

Generally, the present invention provides new processes for the synthesis of substituted benzimidazole compounds.

As a first aspect, the present invention provides a process for preparing a compound of formula I:

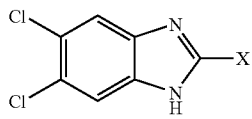

(I)

wherein X is halo. The process comprises the steps of: (a) cyclizing 4,5-dichloro-o-phenylenediamine with carbonyl di-imidazole to yield a compound of formula II:

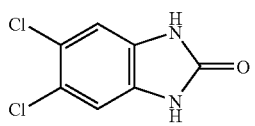

(II)

and
(b) reacting the compound of formula II with $PO(X)_3$ to prepare a compound of formula I.

In a further aspect, the present invention provides a process for preparing 2-bromo-5,6-dichlorobenzimidazole which comprises reacting a 5,6-dichlorobenzimidazole-2-one with phosphorous oxybromide.

In a further aspect of the invention, there is provided a process for preparing a compound of formula VI:

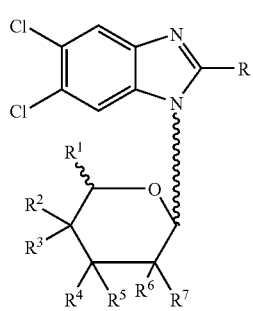

(VI)

wherein R is halo; $R^1$ is hydrogen; each of $R^2$, $R^3$, $R^4$, $R^5$, $R^6$ and $R^7$ is independently selected from the group consisting of H, hydroxy and protected hydroxy group; and pharmaceutically acceptable derivatives and prodrugs thereof. The process comprising the steps of: (a) cyclizing 4,5-dichloro-o-phenylenediamine with carbonyl di-imidazole to yield a compound of formula II:

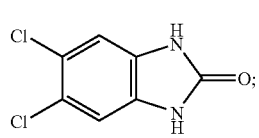

(II)

(b) reacting the compound of formula II with $PO(X)_3$ wherein X is halo, to prepare a compound of formula I:

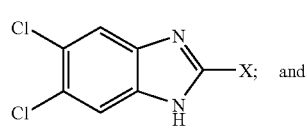

(I); and (c) reacting the compound of formula I with a pyranoside of formula IV:

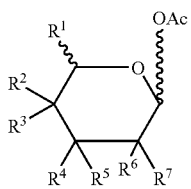

(IV)

to prepare a compound of formula VI and pharmaceutically acceptable derivatives and prodrugs thereof.

In a further aspect of the invention, there is provided a process for preparing 2-bromo-5,6-dichloro-1-β-D-ribopyranosyl-1H-benzimidazole and pharmaceutically acceptable derivatives and prodrugs thereof. The process comprising: (a) reacting 5,6-dichlorobenzimidazol-2-one with phosphorous oxybromide to produce 2-bromo-5,6-dichlorobenzimidazole; (b) reacting 2-bromo-5,6-dichlorobenzimidazole with 1,2,3,4 tetra-O-acetyl-β-D-ribopyranose to produce 2-bromo-5,6-dichloro-1-(2,3,4-tri-O-acetyl)-β-D-ribopyranosyl)-1H-benzimidazole; and (c) deprotecting 2-bromo-5,6-dichloro-1-(2,3,4-tri-O-acetyl)-β-D-ribopyranosyl)-1H-benzimidazole to produce 2-bromo-5,6-dichloro-1-β-D-ribopyranosyl-1H-benzimidazole and pharmaceutically acceptable derivatives and prodrugs thereof. Thus, the present invention provides a process for preparing 2-bromo-5,6-dichloro-1-(2,3,4-tri-O-acetyl)-β-D-ribopyranosyl)-1H-benzimidazole by performing steps (a) and (b) above, without also carrying out step (e) of deprotecting (or removing the O-acetyl protecting groups). The process may further comprise the preliminary step of preparing 5,6-dichlorobenzimidazol-2-one by cyclizing 4,5-dichloro-o-phenylenediamine with carbonyl di-imidazole.

In yet another aspect, the present invention provides a process for preparing compounds of formula VII:

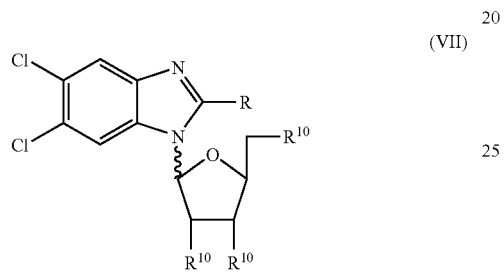

(VII)

wherein:
R is —NR⁸R⁹ where R⁸ and R⁹ are each independently selected from the group consisting of H, $C_{1-6}$alkyl, cyano$C_{1-6}$alkyl, hydroxy$C_{1-6}$alkyl, halo$C_{1-6}$alkyl, $C_{3-7}$cycloalkyl, $C_{1-6}$alkyl$C_{3-7}$cycloalkyl, $C_{2-6}$alkenyl, $C_{3-7}$cycloalkyl$C_{1-6}$alkyl, $C_{2-6}$alkynyl, aryl, aryl$C_{1-6}$alkyl, and $COC_{1-6}$alkyl;
each $R^{10}$ is independently selected from the group consisting of hydroxy and protected hydroxy group; and pharmaceutically acceptable derivatives and prodrugs thereof. The process comprises the steps of: (a) cyclizing 4,5-dichloro-o-phenylenediamine with carbonyl di-imidazole to yield a compound of formula II:

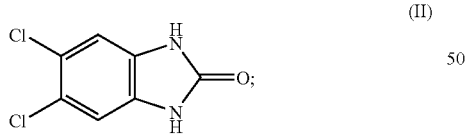

(II)

(b) reacting the compound of formula II with PO(X)₃ wherein X is halo, to prepare a compound of formula I:

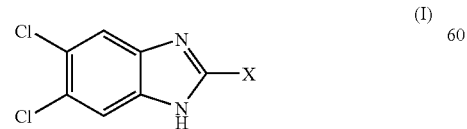

(I)

(c) reacting the compound of formula I with a furanosyl of formula III:

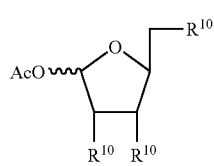

(III)

to prepare a compound of formula V:

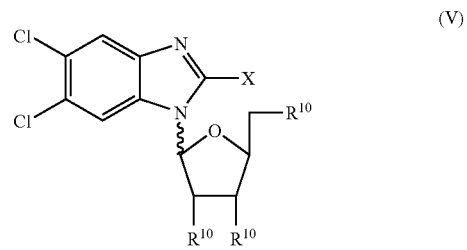

(V)

(d) reacting the compound of formula V with an amine of formula H—NR⁸R⁹; to prepare a compound of formula VII and pharmaceutically acceptable derivatives and prodrugs thereof.

In yet another aspect, the present invention provides a process for preparing compounds of formula X:

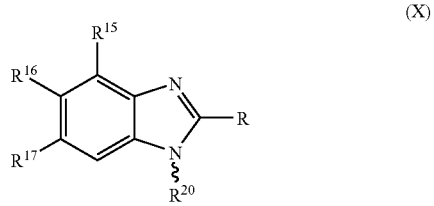

(X)

wherein:
R is selected from the group consisting of halo, hydroxy, azido, $C_{1-8}$alkyl, trihalomethyl, $C_{1-8}$alkoxy, $C_{2-6}$alkenyl, $C_{2-6}$alkynyl, $C_{6-14}$aryl$C_{2-6}$alkenyl, $C_{6-14}$aryl$C_{2-6}$alkynyl, —NR²⁵R¹⁶ wherein R²⁵ and R²⁶ may be the same or different and are each independently selected from the group consisting of H, halo, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl-$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-6}$alkyl, heterocyclyl$C_{1-8}$alkyl, $C_{1-8}$alkylcarbonyl, and $C_{6-14}$aryl-sulfonyl;
—NHNR³⁰R³¹ wherein R³⁰ and R³¹ are the same or different and are each independently $C_{1-6}$alkyl;
—N=NN$C_{1-6}$alkyl;
—NHO$C_{1-6}$alkyl;
—OR²⁷ wherein R²⁷ is selected from the group consisting of $C_{1-8}$alkyl, $C_{3-7}$cyclo-alkyl, and $C_{6-14}$aryl;
—SR²⁸ wherein R²⁸ is selected from the group consisting of H, $C_{1-8}$alkyl, hydroxy$C_{1-8}$alkyl, $C_{3-7}$cycloalkyl, $C_{6-14}$aryl, and $C_{6-14}$aryl$C_{1-6}$alkyl;
R¹⁵ is selected from the group consisting of H, halo, $C_{1-8}$alkyl or $C_{2-6}$alkenyl;
R¹⁶ and R¹⁷ may be the same or different and are each independently selected from the group consisting of H, halo, $C_{1-8}$alkyl, $C_{6-14}$aryl, heterocyclyl$C_{1-8}$aryl, $C_{1-8}$alkoxy, halo$C_{1-8}$alkyl, $NO_2$, and $SR^{29}$ where $R^{29}$ is selected from the group consisting of H, $C_{1-8}$alkyl, $C_{6-14}$aryl or $C_{6-14}$aryl$C_{1-8}$alkyl; and $R^{20}$ is a D- or L-sugar moiety selected from the group consisting of:

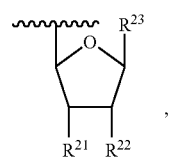

a

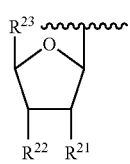

b

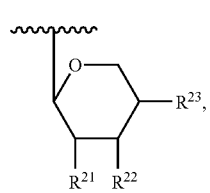

c

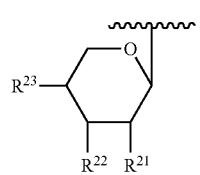

d wherein
$R^{21}$ and $R^{22}$ may be the same or different and are each independently selected from the group consisting of H, hydroxy, protected hydroxy group, halo, $C_{1-8}$alkyl, $C_{1-8}$alkylhydroxy, halo$C_{1-8}$alkyl, or $C_{1-8}$alkoxy;
$R^{23}$ is selected from the group consisting of H, hydroxy, protected hydroxy group, $C_{1-8}$alkyl, $C_{1-8}$-alkoxy, $CH_2R^{32}$ wherein $R^{32}$ is hydroxy, protected hydroxy group, halo, or azido; and $C(R^{33})_3$ wherein each $R^{33}$ is halo;
and wherein $R^{21}$, $R^{22}$ and $R^{23}$ may be in the α- or β-position;

and pharmaceutically acceptable derivatives and prodrugs thereof. The process comprises the steps of:
(a) cyclizing a phenylenediamine of formula XI:

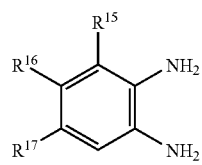

(XI)

with carbonyl di-imidazole to yield a compound of formula XII:

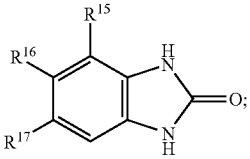

(XII)

(b) reacting the compound of formula XII with $PO(X)_3$, wherein X is halo, to prepare a compound of formula XIII:

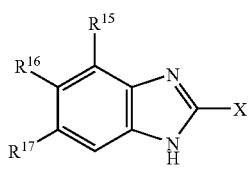

(XIII)

(c) reacting the compound of formula XIII with a 5- or 6-membered, D- or L-sugar selected from the group consisting of:

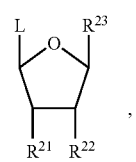

A

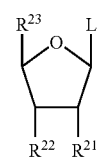

B

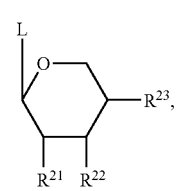

C

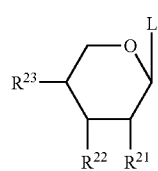

D wherein
L is a leaving group in the α- or β-position to prepare compounds of formula X:

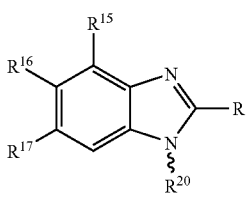

(X)

wherein $R^{15}$, $R^{16}$, $R^{17}$, and $R^{20}$ are as defined above and R is halo, and pharmaceutically acceptable derivatives and prodrugs thereof; and (d) optionally converting the compound of formula X or pharmaceutically acceptable derivative or prodrug thereof into a further compound of formula X or pharmaceutically acceptable derivative or prodrug thereof by nucleophilic substitution.

DETAILED DESCRIPTION OF THE INVENTION

The term "alkyl", alone or in combination with any other term, refers to a straight-chain or branch-chain saturated aliphatic hydrocarbon radical containing the specified number of carbon atoms, or where no number is specified, preferably from 1-10 and more preferably from 1-6 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like, with methyl and ethyl being preferred.

The term "alkenyl," alone or in combination with any other term, refers to a straight-chain or branched-chain mono- or poly-unsaturated aliphatic hydrocarbon radical containing the specified number of carbon atoms, or where no number is specified, preferably from 2-10 carbon atoms and more preferably, from 2-6 carbon atoms. References to alkenyl groups include groups which may be in the E- or Z-form or a mixture thereof and which when they contain at least three carbon atoms, may be branched. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z, E- and Z,Z-hexadienyl and the like.

The term "alkynyl" refers to hydrocarbon groups of either a straight or branched configuration with one or more carbon-carbon triple bonds which may occur in any stable point along the chain, such as ethynyl, propynyl, butynyl, pentynyl, and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like, with methoxy being preferred.

Alkenyl and alkynyl substituents may optionally contain one or more heteroatoms such as nitrogen, sulfur, or oxygen.

The term "aryl," alone or in combination with any other term, refers to a carbocyclic aromatic radical (such as phenyl or naphthyl) containing the specified number of carbon atoms, preferably from 6-14 carbon atoms, and more preferably from 6-10 carbon atoms, optionally substituted with one or more substituents selected from C1-6 alkoxy, (for example methoxy), nitro, halogen, (for example chloro), amino, carboxylate and hydroxy. Examples of aryl radicals include, but are not limited to phenyl, naphthyl, indenyl, indanyl, azulenyl, fluorenyl, anthracenyl and the like.

The term "heterocycle" and "heterocyclic" radical, unless otherwise defined herein, refers to a stable 3-7 membered monocyclic heterocyclic ring or 8-11 membered bicyclic heterocyclic ring which is either saturated or unsaturated, and which may be optionally benzofused if monocyclic. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom which results in the creation of a stable structure. Preferred heterocycles include 5-7 membered monocyclic heterocycles and 8-10 membered bicyclic heterocycles. Examples of such groups include imidazolyl, imidazolinoyl, imidazolidinyl, quinolyl, isoqinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiomorpholinyl, furyl, thienyl, triazolyl, thiazolyl, carbolinyl, tetrazolyl, thiazolidinyl, benzofuranoyl, thiomorpholinyl sulfone, oxazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl; thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetahydrofurodihydrofuranyl, tetrahydropyranodihydrofuranyl, dihydropyranyl, tetrahydrofurofuranyl and tetrahydropyranofuranyl.

Preferred heterocycles include imidazolyl, pyrrolyl, pyrrolinyl, piperidinyl, piperazinyl, and morpholinyl.

The terms "halo" or "halogen" refers to a radical of fluorine, chlorine, bromine or iodine.

The term "halo$C_{1-8}$ alkyl" means a $C_{1-8}$alkyl group in which one or more hydrogens is replaced by halo and preferably containing one, two or three halo groups. Examples of such groups include trifluoromethyl and fluoroisopropyl.

As used herein, the compounds synthesized according to the present invention are defined to include pharmaceutically acceptable derivatives or prodrugs thereof. A "pharmaceutically acceptable derivative" or "pharmaceutically acceptable prodrug" means any pharmaceutically acceptable salt, ester, salt of an ester, or other derivative of a compound described herein which, upon administration to a recipient, is capable of providing (directly or indirectly) a compound described herein or an inhibitorily active metabolite or residue thereof. Particularly favored derivatives and prodrugs are those that increase the bioavailability of the compounds described herein when such compounds are administered to a mammal (e.g., by allowing an orally administered compound to be more readily absorbed into the blood) or which enhance delivery of the parent compound to a biological compartment (e.g., the brain or lymphatic system) relative to the parent species.

The compounds described herein may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectianate, persulfate, phenylproprionate, picrate, pivalate, propionate, succinate, tartrate, thiocyanate, tosylate and undecanoate.

Pharmaceutically acceptable salts of the compounds described herein include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds described herein and their pharmaceutically acceptable acid addition salts.

Salts derived from appropriate bases include alkali metal (e.g. sodium), alkaline earth metal (e.g., magnesium), ammonium and N—W+4 (wherein W is $C_{1-4}$alkyl). Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$alkyl group).

Pharmaceutically acceptable salts include salts of organic carboxylic acids such as ascorbic, acetic, citric, lactic, tartaric, malic, maleic, isothionic, lactobionic, p-aminobenzoic and succinic acids; organic sulfonic acids such as methanesulfonic, ethanesulfonic, benzenesulfonic and p-toluenesulfonic acids and inorganic acids such as hydrochloric, sulfuric, phosphoric, sulfamic and pyrophosphoric acids.

Preferred salts include salts formed from hydrochloric, sulfuric, acetic, succinic, citric and ascorbic acids.

Preferred esters of the compounds described herein are independently selected from the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

In such esters, unless otherwise specified, any alkyl moiety present advantageously contains from 1 to 18 carbon atoms, particularly from 1 to 6 carbon atoms, more particularly from 1 to 4 carbon atoms, Any cycloalkyl moiety present in such esters advantageously contains from 3 to 6 carbon atoms. Any aryl moiety present in such esters advantageously comprises a phenyl group.

Preferred carboxylic acid esters of compounds according to the invention include the acetate, butyrate and valerate esters. L-valyl is a particularly preferred amino acid ester.

Any reference herein to any of the compounds which can be synthesized by the processes of the present invention also includes a reference to a pharmaceutically acceptable derivatives and prodrugs thereof.

The compounds of formula I:

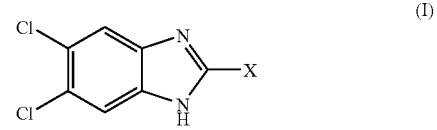

wherein X is halo are useful intermediates for the synthesis of a number of compounds possessing antiviral activity. The compounds of formula I are prepared according to the present invention, by (a) cyclizing 4,5-dichloro-o-phenylenediamine with carbonyl di-imidazole to yield a compound of formula II:

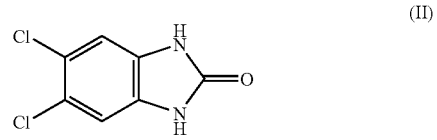

and (b) reacting the compound of formula II with $POX)_3$ to prepare a compound of formula I.

Each step of the reaction is typically carried out in a solvent. For example, step (a) of the foregoing process may be carried out in an aprotic solvent, such as tetrahydrofuran. Step (b) may be carried out in a solvent such as ethyl acetate. Preferably, step (b) is carried out at reflux In one preferred embodiment, the process comprises the further step (c) of crystallizing the compound of formula I from ethyl acetate.

According to a preferred embodiment, the present invention provides a process for preparing compounds of formula I wherein X is Br. According to another embodiment, compounds of formula I wherein X is Cl are synthesized.

According to one preferred embodiment, the present invention provides a process for preparing 2-bromo-5,6-dichlorobenzimidazole which comprises reacting a 5,6-dichlorobenzimidazole-2-one with phosphorous oxybromide. Also according to the present invention, 5,6-dichlorobenzimidazole-2-one is prepared by cyclizing 4,5-dichloro-o-phenylenediamine with carbonyl di-imidazole.

The process of the present invention provides a number of distinct advantages over conventional processes for preparing 2-halo-5,6-dichloro-benzimidazole. The process of the present invention is more reliable and suitable for the large scale synthesis of 2-halo-5,6-dichloro-benzimidazoles than conventional process. For example, a conventional process for the conversion of the 5,6-dichloro-benzimidazole-2-one to the 2-halo-5,6-dichloro-benzimidazole involves a non-aqueous diazotisation which can be capricious and unreliable in large-scale synthesis. The process of the present invention also utilizes milder, less toxic and more environmentally conscious reagents.

Cyanogen bromide is conventionally used for the cyclization of the phenylene diamine; the process of the present invention utilizes carbonyl di-imidazole. The process of the present invention provides the further advantage of improved yield over conventional processes.

The compounds of formula I may serve as intermediates in a process for synthesizing compounds of formula X:

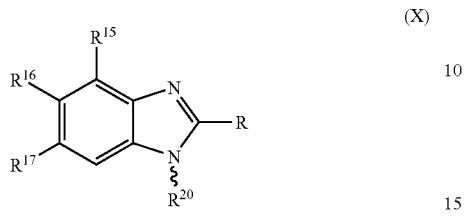

wherein:

R is selected from the group consisting of halo, hydroxy, azido, $C_{1-8}$alkyl, trihalomethyl, $C_{1-8}$alkoxy, $C_{2-6}$alkenyl, $C_{2-6}$alkynyl, $C_{6-14}$aryl$C_{2-6}$alkenyl, $C_{6-14}$aryl$C_{2-6}$alkynyl, —NR$^{25}$R$^{26}$ wherein R$^{25}$ and R$^{26}$ may be the same or different and are each independently selected from the group consisting of H, halo, $C_{1-8}$alkyl, cyano$C_{1-8}$alkyl, hydroxy$C_{1-8}$alkyl, halo$C_{1-8}$alkyl, $C_{3-7}$cycloalkyl, $C_{1-8}$alkyl-$C_{3-7}$cycloalkyl, $C_{2-6}$alkenyl, $C_{3-7}$cycloalkyl$C_{1-8}$alkyl, $C_{2-6}$alkynyl, $C_{6-14}$aryl, $C_{6-14}$aryl$C_{1-6}$alkyl, heterocyclyl$C_{1-8}$alkyl, $C_{1-8}$alkylcarbonyl, and $C_{6-14}$aryl-sulfonyl or R$^{25}$ and R$^{26}$ together with the N atom to which they are attached form a 3, 4, 5, or 6-membered heterocyclic ring;

—NHNR$^{30}$R$^{31}$ wherein R$^{30}$ and R$^{31}$ are the same or different and are each independently $C_{1-6}$alkyl;

—N=NNC$_{1-6}$alkyl;

—NHOC$_{1-6}$alkyl;

—OR$^{27}$ wherein R$^{27}$ is selected from the group consisting of $C_{1-8}$alkyl, $C_{3-7}$cyclo-alkyl, and $C_{6-14}$aryl;

SR$^{28}$ wherein R$^{28}$ is selected from the group consisting of H, $C_{1-8}$alkyl, hydroxy$C_{1-8}$alkyl, $C_{3-7}$cycloalkyl, $C_{6-14}$aryl, and $C_{6-14}$aryl$C_{1-6}$alkyl;

R$^{15}$ is selected from the group consisting of H, halo, $C_{1-6}$alkyl or $C_{2-6}$alkenyl;

R$^{16}$ and R$^{17}$ may be the same or different and are each independently selected from the group consisting of H, halo, $C_{1-8}$alkyl, $C_{6-14}$aryl, heterocyclyl$C_{1-8}$aryl, $C_{1-8}$alkoxy, halo$C_{1-8}$alkyl, NO$_2$, and SR$^{29}$ where R$^{29}$ is selected from the group consisting of H, $C_{1-8}$alkyl, $C_{6-14}$aryl or $C_{6-14}$aryl$C_{1-8}$alkyl; and R$^{20}$ is a D- or L-sugar moiety selected from the group consisting of:

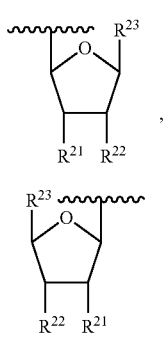

wherein

R$^{21}$ and R$^{22}$ may be the same or different and are each independently selected from the group consisting of H, hydroxy, protected hydroxy group, halo, $C_{1-8}$alkyl, $C_{1-8}$alkylhydroxy, halo$C_{1-8}$alkyl, or $C_{1-8}$alkoxy;

R$^{23}$ is selected from the group consisting of H, hydroxy, protected hydroxy group, $C_{1-8}$alkyl, $C_{1-8}$alkoxy, CH$^2$R$^{32}$ wherein R$^{32}$ is hydroxy, protected hydroxy group, halo, or azido; and C(R$^{33}$)$_3$ wherein each R$^{33}$ is halo;

and wherein R$^{21}$, R$^{22}$ and R$^{23}$ may be in the α- or β-position;

and pharmaceutically acceptable derivatives and prodrugs thereof.

The process for preparing compounds of formula X proceeds generally, according to the following Scheme 1:

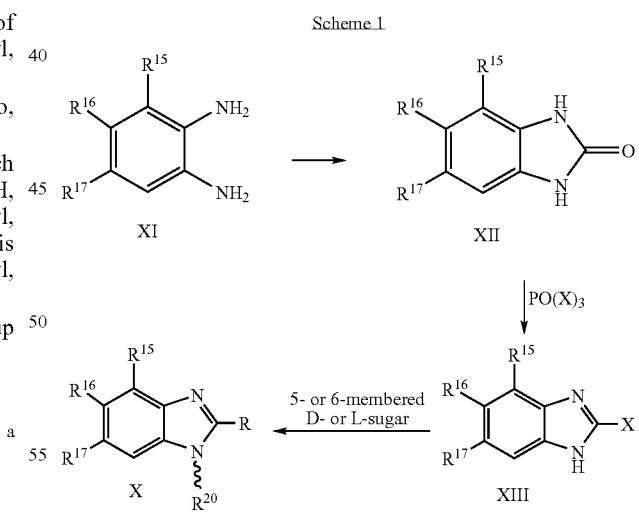

wherein R, R$^{15}$, R$^{16}$, R$^{17}$, R$^{20}$ and X are as defined above.

Generally, the process comprises the steps of: (a) cyclizing the phenylenediamine of formula XI with carbonyl di-imidazole to yield a compound of formula XII; (b) reacting the compound of formula XII with PO(X)$_3$ to prepare a compound of formula XIII; and (c) reacting the compound of formula XIII with a 5- or 6-membered, D- or L-sugar, which is selected from the group consisting of:

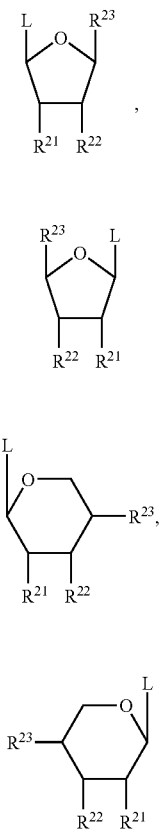

wherein L is a leaving group in the α- or β-position, for example a halo, an alkyl- or aryl-thio (such as phenylthio) or an aryl or aliphatic ester group (such as benzoate or acetate). In one embodiment, L is an acetate leaving group.

The first steps of the process, for the preparation of compounds of formula XIII, are the same as those described hereinabove for the preparation of compounds of formula I. Compounds of formula XIII may be reacted with the 5- or 6-membered D- or L-sugars of formulas A-D to prepare the preferred compounds of formula X wherein R is halo. Processes for coupling the substituted benzimidazole base to the sugar are described in PCT Publication Nos. WO 98/56761, WO 92/07867, WO 96/01833, WO 97/25337, and WO 99/06424, the subject matter of each is incorporated herein by reference in its entirety.

Preferred 5- or 6-membered D- or L-sugars for coupling to the benzimidazole base include the 5-membered D- and L-sugars of formulas A and B and the six-membered D-sugars of formula D. More preferably, the sugar is a 5-membered L-sugar of formula B or the six-membered D-sugar of formula D.

The sugars may be in the α- or β-configuration. Preferred sugars for coupling to the benzimidazole base include β-L-ribofuranosyls, β-D-ribofuranosyls, 5'-deoxy-β-D-ribofuranosyls, β-D-ribopyranosyls, and α-L-lyxofuranosyls. Particularly preferred sugars include β-L-ribofuranosyls and β-D-ribopyranosyls.

As an alternative to the 5- and 6-membered sugars described above, the process of the present invention may also be employed for the synthesis of carbocyclic substituted benzimidazole derivatives by coupling the benzimidazole base of formula XIII to a 5- or 6-membered carbocyclic moiety instead of the sugar. Suitable carbocyclic moieties and processes for coupling a benzimidazole base to a carbocyclic moiety are known in the art.

Optionally, the foregoing process may include one or more additional steps. In one preferred embodiment, the process optionally includes the additional step of (i) converting the compound of formula X to a further compound of formula X. For example, the compound of formula X wherein R is halo may be converted to another compound of formula X wherein R is other than halo.

Generally, the process of converting a compound of formula X wherein R is halo into a further compound of formula X wherein R is other than halo, involves nucleophilic substitution. Methods are known in the art for the conversion of 2-halo benzimidazoles (e.g., compounds of formula X wherein R is halo) to 2-substituted benzimidazoles (e.g., compounds of formula X wherein R is —NR$^8$R$^9$, etc.) by nucleophilic substitution. For example, such methods are described in PCT Publication Nos. WO 98/56761, WO 92/07867, WO 96/01833, WO 97/25337, and WO 99/06424, already incorporated herein by reference. Examples of suitable nucleophiles for reaction with the compound of formula X wherein R is halo include but are not limited to amines, alkoxides, mercaptans, hydrazines, alkylazos, and alkoxyamines. For example, compounds of formula X wherein R is —NR$^8$R$^9$ may be prepared by reacting compounds of formula X wherein R is halo with an amine nucleophile of formula H—NR$^8$R$^9$. Typically the reaction is effected at elevated temperature, 70-80° C. in an organic solvent such as ethanol or dimethyl sulfoxide. Suitable amine nucleophiles are commercially available or are readily prepared by one skilled in the art The process may also optionally include any one or more of the following additional steps, which may be performed in any desired or necessary order:

(ii) removing any remaining protecting group(s) on the compound of formula X (e.g., when any one or more of R$^{21}$, R$^{22}$, and R$^{23}$ is a protected hydroxy group, e.g., O-acetyl);

(iii) converting a compound of formula X into a pharmaceutically acceptable derivative or prodrug thereof;

(iv) converting a pharmaceutically acceptable derivative or prodrug of a compound of formula X into a compound of formula X;

(v) converting a pharmaceutically acceptable derivative or prodrug of a compound of formula X into a further pharmaceutically acceptable derivative or prodrug thereof; and (vi) separating the alpha and beta anomers of the compound of formula X or a pharmaceutically acceptable derivative or prodrug thereof.

Methods for carrying out each of the foregoing optional, additional steps are known in the art and are described in PCT Publication Nos. WO 98/56761, WO 92/07867, WO 96/01833, WO 97/25337, and WO 99/06424, already incorporated herein by reference.

The present invention further provides methods for preparing certain preferred compounds for formula X Preferred compounds of formula X which can be prepared according to the methods of the present invention include but are not limited to compounds of formula VI:

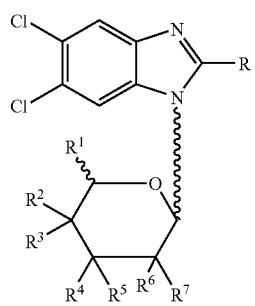

(VI)

wherein R is halo; $R^1$ is hydrogen; and each of $R^2$, $R^3$, $R^4$, $R^5$, $R^6$ and $R^7$ is independently selected from the group consisting of H, hydroxy and protected hydroxy group; and pharmaceutically acceptable derivatives and prodrugs thereof.

More specifically, preferred compounds which can be prepared according to the methods of the present invention include but are not limit to compounds of formula VI wherein the pyranosyl moiety is a β-D pyranosyl; compounds of formula VI wherein $R^2$, $R^4$ and $R^6$ are each hydroxy or O-acetyl; compounds wherein $R^3$, $R^5$, and $R^7$ are each H, and compounds wherein R is Br. Particularly preferred compounds of formula VI include compounds wherein the pyranosyl moiety is a β-D pyranosyl, $R^2$, $R^4$ and $R^6$ are each hydroxy or O-acetyl, $R^3$, $R^5$, and $R^7$ are each H, and R is Br. According to one preferred embodiment of the present invention, 2-bromo-5,6-dichloro-1-β-D-ribopyranosyl)-1H-benzimidazole and pharmaceutically acceptable derivatives and prodrugs thereof is prepared. According to another preferred embodiment, 2-bromo-5,6-dichloro-1-(2,3,5-tri-O-acetyl-β-D-ribopyranosyl)-1H-benzimidazole and pharmaceutically acceptable salts and derivatives thereof are prepared.

Compounds of formula VI can be prepared by a process comprising the steps of:
(a) cyclizing 4,5-dichloro-o-phenylenediamine with carbonyl di-imidazole to yield a compound of formula II:

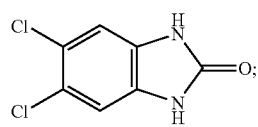

(II)

(b) reacting the compound of formula II with PO(X)$_3$ wherein X is halo, to prepare a compound of formula I:

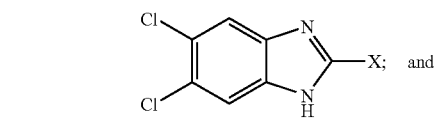

(I)

(c) reacting the compound of formula I with a pyranoside of formula IV:

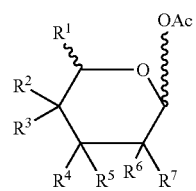

(IV)

wherein each of $R^2$, $R^3$, $R^4$, $R^5$, $R^6$ and $R^7$ is independently selected from the group consisting of H, hydroxy and protected hydroxy group (for example O-acetyl). The acetate leaving group (—OAc) is in the α- or β-position. According to one preferred embodiment of the process, X is Br. According to one preferred embodiment, the pyranoside is a β-D pyranoside.

Steps a) and b) for preparing compounds of formula I are described herein above. Methods for carrying out step c) for coupling the benzimidazole base of formula I to the pyranoside are described in PCT WO No. 98/56761, the disclosure of which is already incorporated by reference in its entirety.

As with processes for preparing compounds of formula X, processes for preparing compounds of formula VI may optionally include one or more additional steps, which may be performed in any desired or necessary order:

(i) converting a compound of formula VI into a further compound of formula VI, such as for example, by the nucleophilic substition at the 2-postion of a 2-halo-5,6dichloro-benzimidazole-pyranoside compound of formula VI;

(ii) removing any remaining protecting group(s) on the compound of formula VI (e.g., when any one or more of $R^1$-$R^7$ is a protected hydroxy group);

(iii) converting a compound of formula VI into a pharmaceutically acceptable derivative or prodrug thereof;

(iv) converting a pharmaceutically acceptable derivative or prodrug of a compound of formula VI into a compound of formula VI;

(v) converting a pharmaceutically acceptable derivative or prodrug of a compound of formula VI into a further pharmaceutically acceptable derivative or prodrug thereof; and (vi) separating the alpha and beta anomers of the compound of formula VI or a pharmaceutically acceptable derivative or prodrug thereof.

The processes for carrying out these additional, optional steps are described above with reference to processes for making compounds of formula X.

The present invention further provides processes for preparing other preferred compounds for formula X. Another preferred class of compounds of formula X include but are not limited to compounds of formula V or VII:

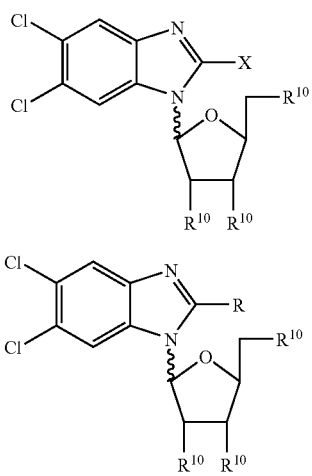

wherein:

X is halo;

R is —NR⁸R⁹ where $R^8$ and $R^9$ are each independently selected from the group consisting of H, $C_{1-6}$alkyl, cyano$C_{1-6}$alkyl, hydroxy$C_{1-6}$alkyl, halo$C_{1-6}$alkyl, $C_{3-7}$cycloalkyl, $C_{1-6}$alkyl$C_{3-7}$cycloalkyl, $C_{2-6}$alkenyl, $C_{3-7}$cycloalkyl$C_{1-6}$alkyl, $C_{2-6}$alkynyl, aryl, aryl$C_{1-6}$alkyl, and COC$_{1-6}$alkyl;

each $R^{10}$ is independently selected from the group consisting of hydroxy and protected hydroxy group;

and pharmaceutically acceptable derivatives and prodrugs thereof.

More specifically, preferred compounds which can be prepared according to the methods of the present invention include but are not limit to compounds of formula VIII wherein one of $R^8$ and $R^9$ is H; compounds wherein $R^8$ is $C_{1-6}$alkyl and $R^9$ is H; compounds wherein R is isopropylamino; compounds wherein the furanosyl moiety:

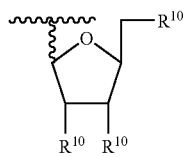

is β-L-ribofuranosyl or α-D-lyxofuranosyl, preferably β-L-ribofuranosyl; compounds wherein each $R^{10}$ is protected hydroxy, preferably O-acetyl; and compounds wherein each $R^{10}$ is hydroxy. Particularly preferred compounds of formula VIII include compounds wherein R is isopropylamino, the furanosyl moiety is β-L-ribofuranosyl, and each $R^{10}$ is protected hydroxy, preferably O-acetyl. Other particularly preferred compounds of formula VII include compounds wherein R is isopropylamino, the furanosyl moiety is β-L-ribofuranosyl, and each $R^{10}$ is hydroxy.

According to one preferred embodiment of the present invention, 2-bromo-5,6-dichloro-1-β-D-ribofuranosyl-1H-benzimidazole and pharmaceutically acceptable derivatives and prodrugs thereof is prepared. According to another preferred embodiment, 2-bromo-5,6-dichloro-1-(2,53,5-tri-O-acetyl-β-D-ribofuranosyl)-1H-benzimidazole and pharmaceutically acceptable derivatives and prodrugs is prepared.

The process for preparing compounds of formula V comprises the steps of: (a) cyclizing 4,5-dichloro-o-phenylenediamine with carbonyl di-imidazole to yield a compound of formula II:

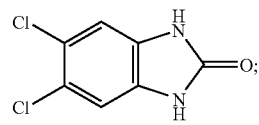

(b) reacting the compound of formula II with PO(X)₃ wherein X is halo, to prepare a compound of formula I:

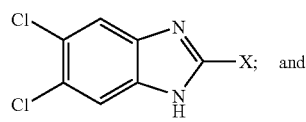

(c) reacting the compound of formula I with a furanosyl of formula III:

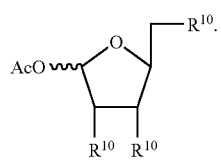

The acetate leaving group (—OAc) is in the α- or β-position.

The process for preparing compounds of formula VII comprises steps (a) through (c) above and the further step (d) of reacting the compound of formula V with an amine of formula H—NR⁸R⁹.

Steps a) and b) for preparing compounds of formula I are described herein above. Methods for carrying out step c) for coupling the benzimidazole base of formula I to the pyranoside are described in PCT WO Nos. 96/01833, 92/07867, 97/25337 and 99/06424, the disclosures of which are already incorporated herein by reference in their entirety.

As with processes for preparing compounds of formula X, processes for-preparing compounds of formula V and VII may optionally include one or more additional steps, which may be performed in any desired or necessary order:

(i) removing any remaining protecting group(s) on the compound of formulas V or VII (e.g., when any one or more $R^{10}$ is a protected hydroxy group);

(ii) converting a compound of formula V or VII into a pharmaceutically acceptable derivative or prodrug thereof;

(iii) converting a pharmaceutically acceptable derivative or prodrug of a compound of formula V or VII into a compound of formula V or VII;

(iv) converting a pharmaceutically acceptable derivative or prodrug of a compound of formula V or VII into a further pharmaceutically acceptable derivative or prodrug thereof; and (v) separating the alpha and beta anomers of the compound of formula V or VII or a pharmaceutically acceptable derivative or prodrug thereof.

According to one preferred embodiment, the present invention provides a process for preparing a compound of formula VII wherein one or more of $R^{10}$ is a protected hydroxy group, and the process further comprises the additional step (i) of removing any protecting groups.

The following examples are intended for illustration only and are not intended to limit the scope of the invention in any way, the invention being defined by the claims which follow.

In the following examples, "g" means grams; "mL" means milliliters; "L" means liters; "mmol" means millimoles; "nm" means nanometers; "h" means hour(s); "° C." means degrees Centigrade; and all percents (%) are in percent by weight unless otherwise noted.

EXAMPLE 1

5,6-Dichloro-(3-dihydro-2H-benzimidazol-2-one

Process A

Carbonyl di-imidazole (75 g, 463 mmol) was added, in portions over 10-15 minutes to a stirred solution of 4,5-dichlorophenylenediamine (72 g, 407 mmol) in tetrahydrofuran (330 mL). The reaction mixture was cooled and stirred at room temperature for 3 h, diluted with water (400 mL), cooled to ca 10° C. and the solid was collected by filtration, washed with water and dried, in vacuo, to give the title compound (84 g, 414 mmol, 98% yield) as a white solid.

Process B

A solution of 4,5-dichlorophenylenediamine (10 g, 56 mmol) in tetrahydrofuran (35 mL) was added slowly to a stirred suspension of carbonyl di-imidazole (9.6 g, 59 mmol) in tetrahydrofuran (10 mL). The resultant suspension was cooled to room temperature, stirred for 1 hour, diluted with water (60 mL) and cooled to ca 5 deg C. The solid was collected by filtration, washed with water and dried, in vacua, to give the title compound (10.9 g, 54 mmol, 950 yield) as a white solid.

EXAMPLE 2

2-Bromo-5,6-dichloro-1H-benzimidazole

Phosphorus oxybromide (211 g, 738 mmol) was added slowly to a stirred suspension of the compound of Example 1 (50 g, 246 mmol) in ethyl acetate (1.25 L). The stirred reaction mixture was heated at reflux for 29 h, cooled to ca 20° C. and then added slowly to water (1 L). The organic phase was separated, washed with water (3 L), treated with charcoal, and evaporated to give a solid which was slurried in a mixture of ethyl acetate:iso-octane (1:1, 200 ml), filtered and dried (50 g, 189 mmol, 77% yield). A portion of the solid (28.5 g) was purified by dissolving in hot ethyl acetate (1.14 L), the resultant solution was clarified by filtration, concentrated to ca 140 ml, cooled to ca 5° C. The product was collected by filtration, washed and dried, in vacua, to give the title compound (22 g) as a white solid.

EXAMPLE 3

2-Bromo-5,6-dichloro-1-(2,3,4-tri-O-acetyl-β-D-ribopyranosyl)-1H-benzimidazole

2-Bromo-5,6-dichlorobenzimidazole (4.0 g, 15 mmol), N,O-bis(trimethylsiyl) acetamide (Aldrich, 3.7 mL, 15 mmol), and 1,2-dichloroethane (Aldrich Sure Seal, 75 mL) were combined and refluxed under nitrogen for 0.5 h. The solution was cooled to room temperature and trimethylsilyl triflate (Aldrich, 3.2 ml, 16 mmol) was added. Immediately, 4.8 g (15 mmol) solid 1,2,3,4-tetra-O-acetyl-b-D-ribopyranose (beta-D-ribopyranose 1,2,3,4-tetraacetate, Aldrich, Milwaukee) was added. The solution was stirred under nitrogen at reflux for 0.5 h, then poured into 7% aqueous sodium bicarbonate and extracted with dichloromethane. The organic layers was dried with magnesium sulfate (anhyd.), filtered, and evaporated. The crude residue was purified on a silica gel column (5×20 cm, 230-400 mesh) with $CH_2Cl_2$ to give 2-bromo-5,6-dichloro-1-(2,3,4tri-O-acetyl-β-D-ribopyranosyl)-1H-benzimidazole which was fractionated in two parts based on elution. The faster product fraction was impure (1.9 g) and purified by a second column to give 1.4 g (2.7 mmol); the slower product fraction was (3.0 g, 5.7 mmol) for a total yield of 56%; m.p. 100-110° C.; $^1$H NMR (DMSO-$d_6$) δ 8.39 (s, 1H), 7.91 (s, 1H), 5.95-5.92 (d, 1H, J=9.6 Hz), 5.73-5.70 (d, 1H, J=9.6 Hz), 5.67 (bs, 2H), 4.13-4.09 (dd, 1H, J=6.3 Hz and J=5.8 Hz), 4.00-3.95 (overlapping dd, 1H), 2.19 (s, 3H), 1.98 (s, 3H), 1.74 (s, 3H).

Anal. Calcd. for $C_{18}H_{17}N_2O_7Cl_2Br$: C, 41.25; H, 3.27; N, 5.34.

Found: C, 41.35; H, 3.28; N, 5.38.

EXAMPLE 4

2-Bromo-5,6-dichloro-1-β-D-ribopyranosyl-1H-benzimidazole 3.0 g (5.7 mmol) 2-Bromo-5,6-dichloro-1-(2,3,4-tri-O-acetyl-β-D-ribopyranosyl) -1H-benzimidazole was deprotected as using the general procedure summarized in the foregoing description by being dissolved in 60 ml dioxane and the resultant solution cooled in an ice bath between 0 and 5° C. To this solution was added all at once, 22 ml (22 mmol) of 1M aq. LiOH. The mixture was removed from the ice bath and allowed to stir at ambient temperature for 1 h. The mixture was diluted with 120 ml of pH 7 phosphate buffer and extracted with ethyl acetate. The ethyl acetate layer was dried over magnesium sulfate (anhyd.), filtered and solvents evaporated. The residue was triturated in dichloromethane and 1.7 g (4.3 mmol, 75% yield) of 2-bromo-5,6-dichloro-1-β-D-ribopyranosyl-1H-benzimidazole was collected by vacuum filtration. The product was dried in a vacuum oven at 50° C. overnight; m.p. 175° C. (decomposes); $^1$H NMR (DMSO-$d_6$) δ 7.96 (s, 1H), 7.07 (s, 1H), 5.64-5.62 (d, J=9.2 Hz), 5.19-5.17 (d, 1H, J=6.4 Hz), 5.13-5.12 (d, 1H, J=3.2 Hz), 4.86-4.84 (d, 1H, J=6.5 Hz), 4.12-4.06 (m, 1H), 3.98-3.92 (m, 2H), 3.68-3.63 (m, 2H).

Anal. Calcd. for $C_{12}H_{11}N_2O_4Cl_2Br$: C, 36.21; H. 2.79; N, 7.04.

Found: C, 36.18; H, 2.91; N, 6.88.

EXAMPLE 5

2-Bromo-5,6-dichloro-1-(2,3,4tri-O-acetyl-D-L-ribofuranosyl)-1H-benzimidazole

2-Bromo-5,6-dichlorobenzimidazole (1.0 g, 3.8 mmol), N,O-bis(trimethylsilyl) acetamide (Aldrich, 0.94 mL, 3.8 mmol), and acetonitrile (Aldrick Sure Seal, 25 mL) were combined and refluxed under nitrogen for 1 h. The solution was cooled to rt and trimethylsilyl triflate (Aldrich, 1.5 mL, 7.6 mmol) was added. After 15 min, solid 1,2,3,4tetra-O-acetyl-L-ribofuranose (1.2 g, 3.8 mmol), prepared by the method of Guthrie and Smith (Chemistry and INdustry, 1968, pp547-548) except that L-ribose was used as the starting material, was added. The solution was stirred under nitrogen at rt for 18 h, then poured into 10% aqueous sodium bicarbonate (100 mL) and extracted with dichloromethan (2×150 mL) The organic layers were dried with magnesium sulfate (anhyd), filtered, and evapoated. The crude residue was purified on a silica gel column (5×20 cm, 230-240 mesh) with 1:30 acetone: $CH_2Cl_2$ to give the title compound (1.2 g, 2.2 mmol, 60%); m.p. 142° C.; $[a]^{20}_D=(+)$ 87.4 (c=0.5 DMF); $UV\lambda_{max}$ (E) pH=7.0: 298 nm (7,600), 289 (7,400), 254 (8,800); 0.1 nNaOH: 298 nm (7,600), 289 (7,400), 256 (7,300); MS (EI): m/z (rel. intensity) 524 (0.15, M+); $^1H$ NMR (DMSO-$d_6$) d 8.08 (s, 1H. Ar—H), 8.01 (s, 1H. Ar—H), 6.22 (d, 1H, H–1', J=7.1 Hz), 5.56 (dd, 1H, H–2', J=7.1 Hz, J=7.2 Hz), 5.45 (dd, 1H, H–3', J=7.2 Hz, J=4.5 Hz), 4.55-4.47 (m, 2H, H–4' and 5'), 4.37 (d, 1H, H–5", J=9.7 Hz), 2.15 (s, 3H, OAc), 2.14 (s, 3H, OAc), 2.01 (s, 3H, OAc).

Anal. Calcd. for $C_{18}H_{17}N_2O_7Cl_2Br$: C, 41.25; H, 3.27; N, 5.34.

Found: C, 41.16; H, 3.39; N, 5.20.

In addition, a small amount of the alpha anomer (2-bromo-5,6-dichloro-1-(2,3,5-tri-O-acetyl-alpha-L-ribofuranosyl)-1H-benzimidazole) was obtained (0.11 g, 0.22 mmol, 6%); m.p. <65° C.; $[a]^{20}_D=(-)206.8$ (c=0.5 DMF); MS (AP+): m/z (rel. intensity): 524 (0.8, M+); $^1H$ NMR (DMSO-$d_6$) d 7.95 (s, 1H, Ar—H), 7.91 (s, 1H, Ar—H), 6.66 (d, 1H, H–1', J=4.2 Hz), 5.68 (t 1H, H–2', J=4.6 Hz), 5.52 (t, 1H, H–3', J=5.9 Hz), 4.87-4.81 (m, 1H, H–4'), 4.37-424 (m, 2H, H–5'), 2.08 (s, 3H, OAc), 2.03 (s, 3H, OAc), 1.51 (s, 3H, OAc).

Anal. Calcd. for $C_{18}H_{17}N_2O_7Cl_2Br$: C, 41.25; H, 3.27; N, 5.34.

Found: C, 41.39; H, 3.35; N, 5.29.

EXAMPLE 6

2-Bromo-5,6-dichloro-1-(β-L-ribofuranosyl)-1H-benzimidazole

Sodium carbonate (0.28 g, 2.65 mmol) and 2-bromo-5,6-dichloro -1-(2,3,5-tri-O-acetyl-p-L-ribofuranosyl)-1H-benzimidazole (1.39 g, 2.65 mmol) were combined with water (4 mL), methanol (20 mL) and ethanol (20 mL) and stirred at rt for 1.5 h. Acetic acid (0.3 mL, 5.3 mmol) was added and the suspension was concentrated to a solid. Purification of the residue on a silica gel column (2.5×20 cm, 230-400 mesh) with 1:9 ethanol:$CH_2Cl_2$ gave the title compound as a white amorphous solid (0.79 g, 2.0 mmol, 75%); m.p. 169° C.; $[a]^{20}_D=(+)105$ (c=0.5 DMF); $UV\lambda_{max}$ (E) pH=7.0: 298 nm (6,700), 289 (6,500), 255 (6,900); 0.1 nNaOH: 298 nm (6,700), 295 (5,400), 256 (6,700); MS (CI): m/z 399 (M+); $^1H$ NMR (DMSO-$d_6$) d 8.57 (s, 1H, Ar—H), 7.96 (s, 1H, Ar—H), 5.89 (d, J=7.9 Hz, H–1'), 5.48 (d, 1H, OH, J=6.3 Hz), 5.42 (t, 1H, OH, J=4.5 Hz), 5.29 (d, 1H, OH, J=4.2 Hz), 4.43 (apparent dd, 1H, H–2', J=13.3 Hz, J=6.1 Hz), 4.14 (apparent t, 1H, H–3', J=4.3 Hz), 4.01 (apparent d, 1H, H–4', J=1.7 Hz), 3.77-3.63 (m, 2H, H–5').

Anal. Calcd. for $C_{12}H_{11}N_2O_4Cl_2Br \cdot 0.20$ $C_2H_{60}$: C, 36.57; H. 3.02; N, 6.8

Found: C, 36.68; H, 2.85; N. 7.05.

EXAMPLE 7

5,6-Dichloro-2-(isoproylamino)-1-(β-L-ribofuranosyl)-1H-benzimidazole soprylamino (10 mL) and 2-bromo-5,6-dichloro-1-(2,3,5-tri-O-acetyl-p-L-ribofuranosyl)-1H-benzimidazole (1.0 g, 1.9 mmol) were combined with absolute ethanol (20 mL) and stirred at 75° C. for 48 h. The reaction mixture was concentrated and purified on a silica gel column (2.5 vm×16 cm, 230-400 mesh) with 1:20 methanol: dichloromethane to give product contaminated with a small amount of higher $R_f$ material. This was repurified on a chromatotron, fitted with a 2 mm silica gel rotor, with 1:25 methanol:dichloromethane to give a white solid (0.43 g, 1.15 mmol, 60%); $[a]^{20}_D=(-) 22.4$ (c=0.5 DMF); $UV\lambda_{max}$ (E): pH 7.0:304 nm (95,00), 275 (1,800) 260 (8,300); 0.1 NaOH: 304 nm (9,900), 275 (19, 00), 260 (8,100); MS (CI): m/z (rel. intensity) 376 (100, M+1); $^1H$ NMR (DMSO-$d_6$) d 7.59 (s, 1H, Ar—H), 7.35 (s, 1H, Ar—H), 6.90 (d, 1H, NH, J=7.8 Hz), 5.73 (d, 1H, H–1', J=6.5 Hz), 5.62 (t, 1H, OH, J=4.2 Hz), 5.27-5.23 (m, 2H, OH), 4.27 (apparent dd, 1H, J=13.4 Hz, J=7.6 Hz), 4.11-3.99 (m, 2H), 3.97 (br. s, 1H), 3.72-3.61 (m, 2H, H–5'), 1.18 (d, 6H, $CH(CH_3)_2$, J=6.6 Hz).

Anal. Calcd. for $C_{15}H_{19}N_3O_4Cl_2 \cdot 1.00H_2O$: C, 45.70; H, 5.37; N, 10.66.

Found: C, 45.75; H, 4.98; N, 10.50.

EXAMPLE 10

5,6-Dichloro-2-(cyclopropylamino)-1-(D-L-ribofuranosyl)-1H-benzimidazole

Cyclopentylamine (5 mL) and 2-bromo-5,6-dichloro-1-(2,3,5-tri-O-acetyl-β-L-ribofuranosyl)-1H-benzimidazole (0.6 g, 1.1 mmol) were combined with absolute ethanol (10 mL) and stirred at 70° C. for 24 h. The reaction mixture was concentrated and purified on a silica gel column (2.5 vm×16 cm, 230-400 mesh) with 1:9 ethanol: dichloromethane to give a white solid (0.27 g, 0.68 mmol, 59%); m.p. 140° C.; $[a]^{20}_D=(-) 24.0$ (c=0.5 DMF); $UV\lambda_{max}$ (E): pH 7.0: 305 nm (12,700), 276 (2,400) 260 (10,600), 245 (7400); 0.1 N NaOH: 305 nm (12,600), 276 (2,200), 260 (9,900), 247 (7,300); MS (CI): m/z (rel, intensity) 402 (100, M+1); $^1H$ NMR (DMSO-$d_6$) d 7.60 (s, 1H, Ar—H), 7.36 (s, 1H, Ar—H), 6.91 (d, 1H, NH, J=6.8 Hz), 5.74 (d, 1H, H–1', J=7.6 Hz), 5.61 (t, 1H, OH, J=4.2 Hz), 5.26 (d, 1H, OH, J=8.1 Hz), 5.23 (d, 1H, OH, J=5.5 Hz), 4.30-4.14 (m, 2H, NHCH, H–2'), 4.05 (apparent t, 1H, H–3', J=4.9 Hz), 3.96 (br. s, 1H, H–4'), 3.72-3.59 (m, 2H, H–5'), 1.91 (br. s, 2H, $CH_2$), 1.66 (br. s, 2H, $CH_2$), 1.52 (br. s, 4H, $CH_2$).

Anal. Calcd. for $C_{17}H_{21}N_3O_4Cl_2 \cdot 0.20H_2O$: C, 50.31; H, 5.31; N, 10.38.

Found: C, 50.13; H, 5.31; N, 10.05.

In the claims:

1. A process for preparing a compound of formula I:

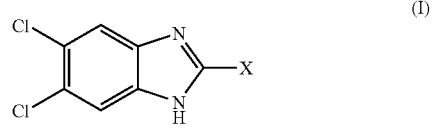

(I)

wherein X is halo,
said process comprising the steps of:
(a) cyclizing 4,5-dichloro-o-phenylenediamine with carbonyl di-imidazole to yield a compound of formula II:

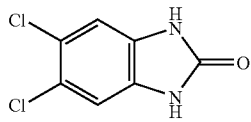

and (b) reacting the compound of formula II with PO(X)$_3$ to prepare a compound of formula I.

2. The process according to claim 1, wherein X is Br.

3. A process for preparing 2-bromo-5,6-dichlorobenzimidazole, said process comprising reacting a 5,6-dichlorobenzimidazole -2-one with phosphorous oxybromide.

4. A process for preparing 2-bromo-5,6-dichloro-1-β-D-ribopyranosyl-1H-benzimidazole said process comprising:

(a) reacting 5,6-dichlorobenzimidazol-2-one with phosphorous oxybrom ide to produce 2-bromo-5,6-dichlorobenzimidazole;

(b) reacting 2-bromo-5,6-dichlorobenzimidazole with 1,2,3,4-tetra-O-acetyl-β-D-ribopyranose to produce 2-bromo-5,6-dichloro-1-(2,3,4-tri-O-acetyl)-β-D-ribopyranosyl) -1H-benzimidazole; and (c) deprotecting 2-bromo-5,6-dichloro-1-(2,3,4-tri-O-acetyl)-β-D-ribopyranosyl) -1H-benzimidazole to produce 2-bromo-5,6-dichloro-1-β-D-ribopyranosyl -1H-benzimidazole.

5. The process according to claim 4, further comprising the step of preparing 5,6-dichlorobenzimidazol-2-one by cyclizing 4,5-d ichloro-o-phenylenediamine with carbonyl di-imidazole.

* * * * *